(12) United States Patent  
Lee et al.

(10) Patent No.: US 8,304,527 B2  
(45) Date of Patent: Nov. 6, 2012

(54) KIT FOR HIGH THROUGHPUT MUTATION SCREENING METHODS

(76) Inventors: Ming-Sheng Lee, Sugar Land, TX (US); Chung-Han Lee, Sugar Land, TX (US); Jeffery Lee, Sugar Land, TX (US)

( * ) Notice: Subject to any disclaimer, the term of this patent is extended or adjusted under 35 U.S.C. 154(b) by 0 days.

(21) Appl. No.: 13/078,800

(22) Filed: Apr. 1, 2011

(65) Prior Publication Data

US 2012/0003638 A1     Jan. 5, 2012

Related U.S. Application Data

(62) Division of application No. 12/151,650, filed on May 8, 2008, now Pat. No. 7,947,446.

(60) Provisional application No. 60/932,094, filed on May 29, 2007.

(51) Int. Cl.
*C07H 21/04* (2006.01)
*C12P 19/34* (2006.01)

(52) U.S. Cl. ..................... 536/24.3; 435/91.1

(58) Field of Classification Search .................. 435/91.1; 536/24.3

See application file for complete search history.

(56) References Cited

U.S. PATENT DOCUMENTS 6,828,098 B2 * 12/2004 Langmore et al. .............. 435/6.1

* cited by examiner

*Primary Examiner* — Kenneth R. Horlick
(74) *Attorney, Agent, or Firm* — DLC Patents, PLLC; Dustin L. Call

(57) ABSTRACT

One example embodiment includes a kit to execute a method of simultaneously screening for genetic mutations in different genes in a multitude of samples. The kit includes an antisense deoxyribonucleic acid (DNA) probe, where the antisense DNA probe will be mixed with a strand of a ribonucleic acid (RNA) to be tested to form a heteroduplex molecule within a sample. The kit also includes a ribonuclease enzyme, an RNA-primed DNA polymerase, a single strand-specific nuclease, DNA-dependent DNA polymerase, a blocking adapter and a tagged reporter adapter. Through ribonuclease digestion, differential sequence fill-in (DSF) and full-length sequence extension, tagged mutant-dual adapter hybrids are formed for detection, quantification or amplification. The sequence ubiquity of said mutant-dual adapter hybrids enables the use of universalized primers for sequence amplification regardless of the numbers or the origins of the mutations involved.

20 Claims, 8 Drawing Sheets

RNA Samples or Transcript Amplification Products Equally Divided into Four Aliquots
A Set of Four Antisense DNA Probes Carrying a 5' "Deoxy-T" Overhang Are Immobilized on Solid Phase Media in Duplicates and in Array Format (Raw "A" and Raw "B" Are Identical)

```
        T  T  T  T  T  T
        1  2  3  4  5 ......N
   A  [ O  O  O  O  O  O ]
   B  [ O  O  O  O  O  O ]
        T  T  T  T  T  T
```

Hybridization
Ribonuclease Digestion

↓ Formation of RNA:DNA Heteroduplexes with a 5' "Deoxy-T" Overhang
  Sequence Extension by an RNA-primed DNA Polymerase and dATP;
  Creating a 3' Single Nucleotide "deoxy-A" Overhang on the Sense Strand ↓ Ligation with a Blocking Adapter Carrying a 3' Single Nucleotide "Deoxy-T"
  Overhang on Its Antisense Strand and Dual (5' and 3') Phosphorylations on Its
  Sense Strand

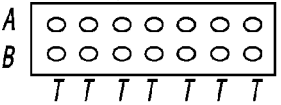

```
   Phos Phos Phos Phos Phos  Phos
    1    2    3    4    5 ......N
A [ O    O    O    O    O    O ]
B [ O    O    O    O    O    O ]
   Phos Phos Phos Phos Phos  Phos
```

↓ DSF with dATP, dCTP, dGTP, and dTTP, Respectively

↓ Single Strand-specific Nuclease Digestion to Hydrolyze Heteroduplexes That Are Filled in Partially ↓ Sequence Extension Using a DNA-dependent DNA Polymerase and All Four dNTPs

```
    A  Phos A  A  Phos Phos
    1   2   3  4   5 ......N
A [ O   O   O  O   O   O ]
B [ O   O   O  O   O   O ]
    A  Phos A  A  Phos Phos
```

At Positions A1(B1), A3(B3), and A4(B4), Nicked Mutant Heteroduplexes Are Filled in with a Complementary dNTP, Resulting in Full Protection from Single Strand-specific Nuclease Digestion and Enabling Full-length Sequence Extension to Replace Downstream RNA, the Sense Strand of the Blocking Adapter, and the Creation of a 3' Single Nucleotide "Deoxy-A" Overhang (As Highlighted by "A")
All Others Remain Blocked by Adapters (As Labeled by "Phos")

↓ Ligation with a Tagged Reporter Adapter

```
       1  2  3  4  5 ... N
   A [ ●  O  ●  ●  O  O ]
   B [ ●  O  ●  ●  O  O ]
```

Formation of Tagged Mutant-Dual Adapter Hybrids at Positions A1(B1), A3(B3) and A4(B4) Where Mutants Are Identified/Quantified by the Tag of the Reporter Adapter. Positive Signals May Be Augmented by Signal Enhancement Methods Targeting the Tagged Reporter Adapter or Mutant-Dual Adapter Hybrids.

FIG. 3

Extraction of Viral RNAs from Tested Samples
Transcript Amplification of the HIV-1 Pol Gene Preparing Various Clades of Antisense pol cDNA Probes
That Carry an Extra "Deoxy-T" at 5'; Probes are Mixed and
Immobilized in Streptavidin-coated Microtiter Wells Dividing Each Samples into Four Aliquots

Antisense DNA Probe T-5'

Applying Each Aliquot to a Microtiter Well

↓ Hybridization

Washing in an Automated Microtiter Plate Washer

↓ Ribonuclease Digestion

Formation of RNA:DNA Heteroduplexes with a 5' "Deoxy-T" Overhang in Samples Harboring HIV-1 Virons Washing in an Automated Microtiter Plate Washer ↓ Sequence Extension Using an RNA-primed DNA Polymerase and dATP Creation of a 3' Single Nucleotide "Deoxy-A" Overhang in Samples Harboring HIV-1 Virons Washing in an Automated Microtiter Plate Washer ↓ Ligation with a Blocking Adapter Carrying an Embedded Restriction Enzyme (RES) Site Samples without HIV-1    Fully Matched Heteroduplex    Partially Matched Heteroduplex    Point Mismatched Heteroduplex

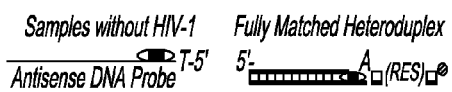 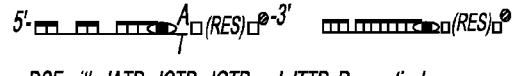

Washing in an Automated Microtiter Plate Washer

↓ DSF with dATP, dCTP, dGTP and dTTP, Respectively (Using dCTP as a Representative)

Washing in an Automated Microtiter Plate Washer

↓ Single Strand-specific Nuclease Digest to Hydrolyze Partially Protected Heteroduplexes Fully Matched Wild-Type        Partially Filled Heteroduplex    Point Mismatches Filled in with a
Samples without HIV-1  Heteroduplex without Fill-in    Becoming Fragmented           Complementary dCTP Is Protected

 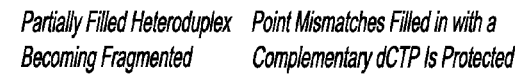

Washing in an Automated Microtiter Plate Washer

↓ Full-Length Sequence Extension and Creation of a 3' "Deoxy-A" Overhang in Mutants Filled in with a Complementary dCTP

Washing in an Automated Microtiter Plate Washer

↓ Ligation with a Tagged Reporter Adapter

Samples without HIV-1    Full Protection by Same        Fragmented Heteroduplex       Full Protection of HIV-1 Mutants
                         Clade of Wild-Type HIV-1       in Different Clade of HIV1    As a Result of Complete Fill-in

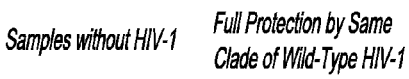 

Formation of Mutant-Dual Adapter Hybrid

Washing in an Automated Microtiter Plate Washer

↓ "RES" Digest to Release Dual Adapter Ligation Products

↓ Amplification of Dual Adapter Ligation Products

FIG. 5    Sensitive Detection and Quantification of Low Frequency Mutants

Sensitivity in Mutation Detection
by
DSF-Enabled Sequential Adapter Ligation and Amplification M: φx174 HaeIII Molecular Weight Markers
1: KG1 Myeloid Leukemia Cells
2: KG1 Leukemia Cells, 1:10
3: KG1 Leukemia Cells, $1:10^2$
4: KG1 Leukemia Cells, $1:10^3$
5: KG1 Leukemia Cells, $1:10^4$
6: KG1 Leukemia Cells, $1:10^5$
7: KG1 Leukemia Cells, $1:10^6$
8: Normal Blood Sample

SEQUENCE LISTING

<160> NUMBER OF SEQ ID NOS: 18

<210> SEQ ID NO 1
<211> LENGTH: 20
<212> TYPE: DNA
<213> ORGANISM: Homo sapiens

<400> SEQUENCE: 1
ggcctgctga aaatgactga                                            20

<210> SEQ ID NO 2
<211> LENGTH: 19
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native K-ras sequence. The extra "TT"
      permits sequence extension by nucleotide "A". Moreover, the "T"
      at position #1 is biotinylated to allow immobilization on solid
      phase media.

<400> SEQUENCE: 2
ttctccccag tcctcatgt                                             19

<210> SEQ ID NO 3
<211> LENGTH: 20
<212> TYPE: DNA
<213> ORGANISM: Homo sapiens

<400> SEQUENCE: 3
gtctgggctt cttgcattgt                                            20

<210> SEQ ID NO 4
<211> LENGTH: 22
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native TP53 sequence. The extra "TT"
      permits sequence extension by nucleotide "A". Moreover, the "T"
      at position #1 is biotinylated to allow immobilization on solid
      phase media.

<400> SEQUENCE: 4
ttcccttctg tcttgaacat ga                                         22

<210> SEQ ID NO 5
<211> LENGTH: 20
<212> TYPE: DNA
<213> ORGANISM: Homo sapiens

<400> SEQUENCE: 5
tgggatcctc atcaagcgac                                            20

<210> SEQ ID NO 6
<211> LENGTH: 22
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native Erb-b2 sequence. The extra "TT"

-continued permits sequence extension by nucleotide "A". Moreover, the "T"
at position #1 is biotinylated to allow immobilization on solid
phase media.

<400> SEQUENCE: 6
ttgtcatcag ctcccacaca gt                                              22

<210> SEQ ID NO 7
<211> LENGTH: 20
<212> TYPE: DNA
<213> ORGANISM: Homo sapiens

<400> SEQUENCE: 7
gagcaatgcg aatacctgtc                                                 20

<210> SEQ ID NO 8
<211> LENGTH: 22
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native VEGFR3 sequence. The extra "TT"
      permits sequence extension by nucleotide "A". Moreover, the "T"
      at position #1 is biotinylated to allow immobilization on solid
      phase media.

<400> SEQUENCE: 8
ttccagcagt tcagcatgat gc                                              22

<210> SEQ ID NO 9
<211> LENGTH: 20
<212> TYPE: DNA
<213> ORGANISM: Homo sapiens

<400> SEQUENCE: 9
ttaggactct agtggcacac                                                 20

<210> SEQ ID NO 10
<211> LENGTH: 21
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native MSH6 sequence. The extra "TT"
      permits sequence extension by nucleotide "A". Moreover, the "T"
      at position #1 is biotinylated to allow immobilization on solid
      phase media.

<400> SEQUENCE: 10
ttcaggaaaa cgaccttcag g                                               21

<210> SEQ ID NO 11
<211> LENGTH: 20
<212> TYPE: DNA
<213> ORGANISM: Homo sapiens

<400> SEQUENCE: 11
ctgactgtag atgatcagtc                                                 20

<210> SEQ ID NO 12
<211> LENGTH: 22
<212> TYPE: DNA
<213> ORGANISM: Homo sapiens
<220> FEATURE:

```
<221> NAME/KEY: misc_feature
<222> LOCATION: (1)..(2)
<223> OTHER INFORMATION: The nucleotide "T" at the positions #1 and #2
      are not present in the native CHEK2 sequence. The extra "TT"
      permits sequence extension by nucleotide "A". Moreover, the "T"
      at position #1 is biotinylated to allow immobilization on solid
      phase media.

<400> SEQUENCE: 12
ttggtagagc tgtggattca tt                                              22

<210> SEQ ID NO 13
<211> LENGTH: 20
<212> TYPE: DNA
<213> ORGANISM: Homo sapiens

<400> SEQUENCE: 13
agcttacccg tcacagcttg                                                 20

<210> SEQ ID NO 14
<211> LENGTH: 24
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native BRIP1 sequence. The extra "TT"
      permits sequence extension by nucleotide "A". Moreover, the "T"
      at position #1 is biotinylated to allow immobilization on solid
      phase media.

<400> SEQUENCE: 14
ttgtctgtaa tgtgtgtgct gatc                                            24

<210> SEQ ID NO 15
<211> LENGTH: 18
<212> TYPE: DNA
<213> ORGANISM: Homo sapiens

<400> SEQUENCE: 15
tatggacacg ttcatcca                                                   18

<210> SEQ ID NO 16
<211> LENGTH: 23
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native LKB1 sequence. The extra "TT"
      permits sequence extension by nucleotide "A". Moreover, the "T"
      at position #1 is biotinylated to allow immobilization on solid
      phase media.

<400> SEQUENCE: 16
ttgtcctgag tgtagatgat gtc                                             23

<210> SEQ ID NO 17
<211> LENGTH: 18
<212> TYPE: DNA
<213> ORGANISM: Homo sapiens

<400> SEQUENCE: 17
aattggagat cgtcacaa                                                   18

<210> SEQ ID NO 18
```

-continued

```
<211> LENGTH: 22
<212> TYPE: DNA
<213> ORGANISM: Homo sapiens
<220> FEATURE:
<221> NAME/KEY: misc_feature
<222> LOCATION: (1)..(2)
<223> OTHER INFORMATION: The nucleotide "T" at the positions #1 and #2
      are not present in the native PIK3CA sequence. The extra "TT"
      permits sequence extension by nucleotide "A". Moreover, the "T"
      at position #1 is biotinylated to allow immobilization on solid
      phase media.

<400> SEQUENCE: 18
tttcggtctt tgcctgctga ga                                              22
```

KIT FOR HIGH THROUGHPUT MUTATION SCREENING METHODS

CROSS-REFERENCE TO RELATED APPLICATIONS

This application is a divisional of and claims the benefit of and priority to U.S. patent application Ser. No. 12/151,650 filed on May 8, 2008 (now U.S. Pat. No. 7,947,446), which application is incorporated herein by reference in its entirety.

U.S. patent application Ser. No. 12/151,650 claims priority to U.S. Provisional Patent Application Ser. No. 60/932,094, filed on May 29, 2007, which application is incorporated herein by reference in its entirety.

INCORPORATION OF SEQUENCE LISTING

This application contains a Sequence Listing in paper form. The computer-readable form (CRF) has been previously submitted in U.S. patent application Ser. No. 12/151,650 filed on May 8, 2008, which sequence listing is incorporated herein by reference in its entirety. In accordance with 37 C.F.R. 1.821(e), please use the CRF filed in the parent application as the CRF for this application. The information recorded in computer readable form is identical to the written sequence listing.

BACKGROUND OF THE INVENTION

1. Technical Field

The present disclosure relates to methods and products that facilitate simultaneous detection of multiple genetic alterations in multiple different genes.

2. Background Information

Genetic mutations play a key role in the pathogenesis, progression and drug resistance of cancer and various infectious diseases. Although some genes have a predilection for involvement in certain cancers and drug-induced mutations, there is significant variation among patients, and multiple different genes could be involved. This underscores the need for a simple method that facilitates simultaneous examination of multiple genes. However, such a goal is very difficult to accomplish due to the complexity of the human genome and the presence of sequence homologues. In order to assure the specificity of mutation detection and enhance sensitivity, current assays require sequence-specific amplification for each target of interest. Likewise, mutations conferring drug resistant microorganisms vary among patients, and various microorganism subtypes can have similar clinical presentations. As a result, screening for mutations in infectious microorganisms also requires laborious multiple amplifications and sequencing. Moreover, the sensitivity of most assays is limited to approximately 1-10%. Therefore, the presence of mutants with a low incidence cannot be detected unless a more sensitive assay becomes available.

The present disclosure describes a universalized strategy for simultaneous screening of a multitude of multiple different genetic regions of interest through the use of two ubiquitous adapters designated as a "blocking adapter" and a "reporter adapter," respectively. In normal wild-types, the blocking adapter is the sole adapter being ligated. In the presence of mutants, sequential ligation of the blocking adapter and the reporter adapter is enabled by differential sequence fill-in (DSF) with a complementary deoxyribonucleotide triphosphate (dNTP), followed by protection from single-stranded DNA-specific nuclease digestion and full-length sequence extension. This leads to the displacement of downstream RNA and the sense strand of the blocking adapter, allowing the creation of a 3' overhang for ligation with the reporter adapter to form mutant-dual adapter hybrids. Mutants and homologous sequences that are not completely filled in with complementary dNTPs are digested into fragments by single-strand-specific nuclease, thereby preventing them from undergoing full-length sequence extension and ligation with the reporter adapter. By targeting the reporter adapter or mutant-dual adapter hybrids, mutants filled in with a complementary dNTP are detected/quantified or amplified for sensitive detection of low frequency mutants. Of note is that all different mutant-dual adapter hybrids share the same sequence at the dual adapter ligation site regardless of the origin or the number of mutations involved. Therefore, mutation detection may be easily augmented by polymerase chain reaction (PCR) with the use of just two ubiquitous primers: one derived from the blocking adapter and the other from the reporter adapter. Likewise, other sequence amplification methods, such as ligase chain reaction (LCR) or transcription-mediated amplification (TMA), may also be directed to target the commonly shared sequence. Without the need of multiple target-specific sequence amplifications, the methods described in this disclosure make it a simple task to perform high throughput mutation screening for a multitude of multiple different genes in a multitude of multiple different samples.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a kit to execute a method of simultaneously screening for genetic mutations in different genes in a multitude of samples. The kit includes an antisense deoxyribonucleic acid (DNA) probe, where the antisense DNA probe will be mixed with a strand of a ribonucleic acid (RNA) to be tested to form a heteroduplex molecule within a sample. The sample forms a first population of fully hybridized wild-type heteroduplexes, a second population of mutant heteroduplexes having a single unhybridized ribonucleotide and a third population of homologous heteroduplexes having at least one stretch of two or more unhybridized ribonucleotides. The kit also includes a blocking substrate, wherein the blocking substrate is configured to protect a 3' end of the RNA strand.

Another example embodiment includes a kit to execute a method of simultaneously screening for genetic mutations in different genes in a multitude of samples. The kit includes an antisense deoxyribonucleic acid (DNA) probe, where the antisense DNA probe will be mixed with a strand of a ribonucleic acid (RNA) to be tested to form a heteroduplex molecule within a sample. The sample forms a first population of fully hybridized wild-type heteroduplexes, a second population of mutant heteroduplexes having a single unhybridized ribonucleotide and a third population of homologous heteroduplexes having at least one stretch of two or more unhybridized ribonucleotides. The kit also includes a blocking adapter, where the blocking adapter is configured to protect the 3' single nucleotide overhang on the RNA strand. The kit further includes a ribonuclease enzyme, where the ribonuclease enzyme is configured to cleave the unhybridized ribonucleotides in the second population and the third population and exposes a 3' hydroxyl group at the cleavage sites. The kit additionally includes an RNA-primed DNA polymerase, where the RNA-primed DNA polymerase is configured to create a second sample performing differential sequence fill-in at the cleaved sites. The kit also includes a single-strand-specific nuclease, where the single-strand-specific nuclease is configured to digest the unprotected deoxyribonucleotides in the third population and in the second population not filled in with a complementary dNTP. The first population and heteroduplexes in the second population filled in with a complementary dNTP are undigested.

Another example embodiment includes a kit to execute a method of simultaneously screening for genetic mutations in different genes in a multitude of samples. The kit includes an antisense deoxyribonucleic acid (DNA) probe, where the antisense DNA probe will be mixed with a strand of a ribonucleic acid (RNA) to be tested to form a heteroduplex molecule within a sample. The sample forms a first population of fully hybridized wild-type heteroduplexes, a second population of mutant heteroduplexes having a single unhybridized ribonucleotide and a third population of homologous heteroduplexes having at least one stretch of two or more unhybridized ribonucleotides. The kit also includes a blocking adapter, where the blocking adapter is configured to protect the 3' single nucleotide overhang on the RNA strand. The kit further includes a ribonuclease enzyme, where the ribonuclease enzyme is configured to cleave the unhybridized ribonucleotides in the second population and the third population and exposes a 3' hydroxyl group at the cleavage sites. The kit additionally includes an RNA-primed DNA polymerase, where the RNA-primed DNA polymerase is configured to create a second sample performing differential sequence fill-in at the cleaved sites. The kit also includes a single-strand-specific nuclease, where the single-strand-specific nuclease is configured to digest the unprotected deoxyribonucleotides in the third population and in the second population not filled in with a complementary dNTP. The first population and heteroduplexes in the second population filled in with a complementary dNTP are undigested. The kit further includes a DNA-dependent DNA polymerase, where the DNA-dependent DNA polymerase is used with all four dNTPs to create a full-length sequence extension in the second population that has been filled in with a complementary dNTP and a new 3' single nucleotide overhang carrying a free 3'-hydroxyl group that is unprotected. The kit additionally includes a tagged reporter adapter, where the tagged reporter adapter is configured to link to the unprotected overhang to form marked mutant-dual adapter hybrids. The kit also includes a detector, where the detector is configured to detect the marked mutant-adapter hybrids.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 3 provides an overview of a non-limiting method for the detection of genetic mutations in microarray format covering a multitude of multiple different genes;

FIG. 5 provides an overview of a non-limiting method for detecting low frequency drug resistant HIV-1 mutants;

DETAILED DESCRIPTION OF SOME EXAMPLE EMBODIMENTS

Figure 1A:
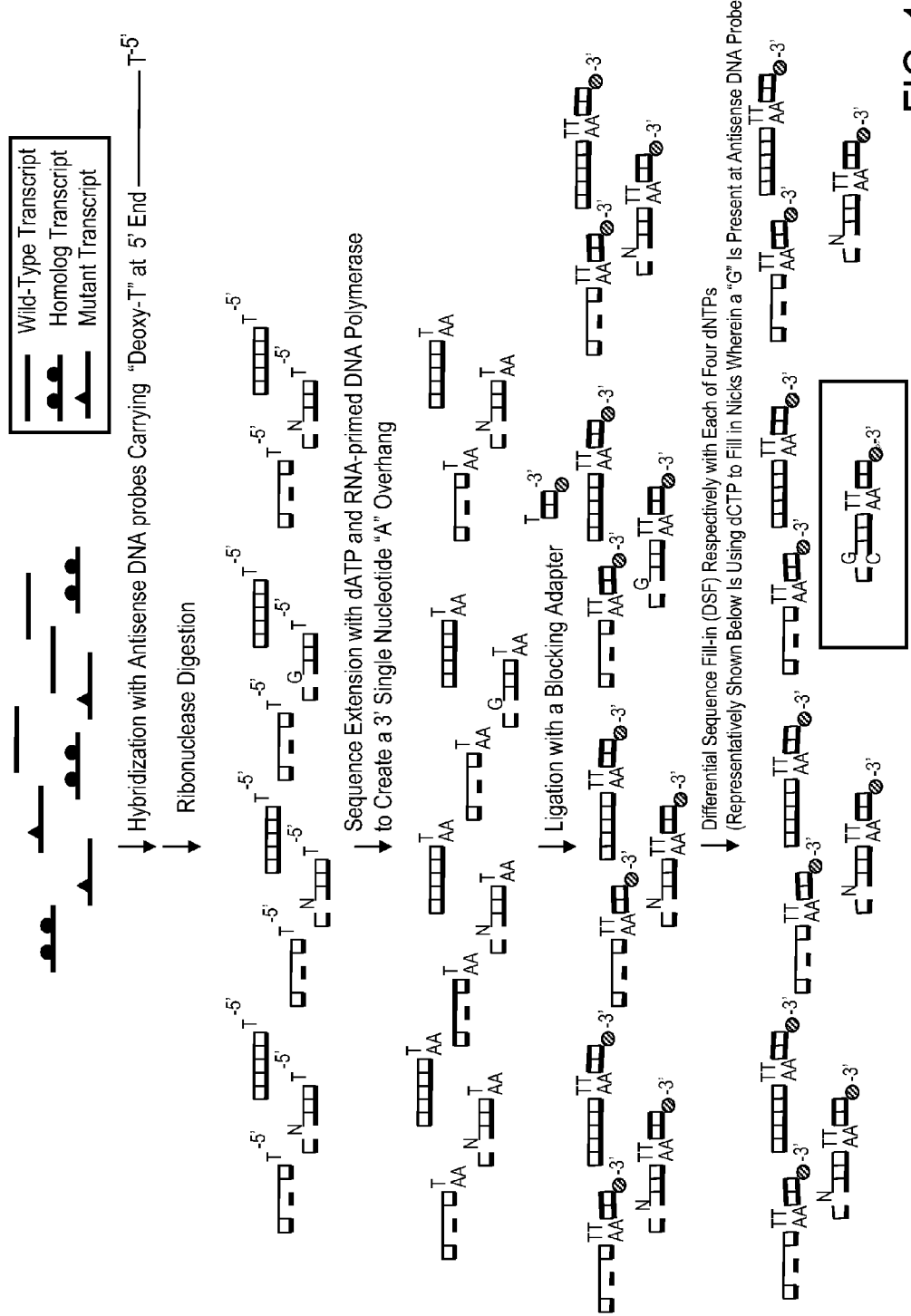
FIG. 1 provides an overview of a series of molecular reactions described in the present disclosure that facilitates simultaneous detection of multiple genetic alterations in a multitude of multiple different targets of interest.

Reference will now be made to the figures wherein like structures will be provided with like reference designations. It is understood that the figures are diagrammatic and schematic representations of some embodiments of the invention, and are not limiting of the present invention, nor are they necessarily drawn to scale.

The methods of the present disclosure facilitate simultaneous detection of one or more genetic mutations residing within a multitude of multiple different genes, nucleic acids (DNAs or RNAs), genetic markers or infectious microorganisms. Through the creation of commonly shared adapter ligation products in mutants of all different origins, mutants may be easily identified and/or quantified regardless of the source, the number, or the nature of mutations involved. A unique feature of the mutation screening methods in the present disclosure is the use of a set of two ubiquitous adapters designated as a "blocking adapter" and a "reporter adapter", respectively. Another unique feature is a molecular reaction named "Differential Sequence Fill-in (DSF)." Sequential utilization of DSF with one or two dNTP(s), single-strand-specific nuclease digestion, and then sequence extension with all four dNTPs results in full-length sequence extension and permits the ligation of the blocking adapter with the reporter adapter to form mutant-dual adapter hybrids solely in mutants that are filled in with a complementary dNTP by DSF. In contrast, wild-type targets, homologous sequences and mutants not filled in with a complementary dNTP remain blocked by the blocking adapter. Consequently, mutants may be identified easily by targeting the tag of the reporter adapter using any applicable signal detection/quantification or enhancement method. Moreover, to detect low frequency mutants easily, sequence amplification of mutant-dual adapter hybrids may be performed with a set of two ubiquitous primers: one specific for the blocking adapter and the other specific for the reporter adapter. This permits simultaneous examination of a multitude of multiple different targets of interest without the need of multiple different target-specific sequence amplifications. As used herein, the term "genetic mutation(s)" include(s) all genetic alterations known in the art, for example but not limited to, point mutation, single nucleotide sequence polymorphism (SNP), deletion, insertion, microsatellite instability, microsatellite sequence polymorphism, translocation, and any combinations thereof. Genetic mutation(s) may be in any region of any genetic material in the genome of human beings, livestock, plants or microorganisms, such as within and/or near any one or more gene(s), and may be within and/or near any coding or noncoding region. The genetic material may be deoxyribonucleic acid (DNA), ribonucleic acid (RNA), or both, and may be any size. The mutation(s) may be associated, directly or indirectly, with a medical condition, for example but not limited to, a cancer, a hereditary disorder, or an infectious disease. In one non-limiting embodiment, the mutation(s) is associated with any stage of initialization, development, progression, and/or remission of any cancer. The mutation(s) may be a marker for a disease or an infectious microorganism. The mutation(s) may be associated with a resistance to therapy, for example resistance to any pharmaceutical compound, drug or biological response modifier, resistance to any type of radiotherapy or immunotherapy, and any combinations thereof. Thus, the methods and products of the present disclosure may be utilized for any one or more of these situations but are by no means limited to these situations.

Nucleic acid (either RNA or DNA) from any source may be used in the methods and products of the present disclosure. The nucleic acid samples may be obtained from any one or more individuals, livestock, plants, and/or microorganisms. The nucleic acid samples may be isolated from any cell, tissue or fluid, including but not limited to, skin, plasma, serum, spinal fluid, lymphatic fluid, synovial fluid, urine, tears, blood cells, organs, tumors, any biopsy sample, a tissue section sample, a cell preparation sample, and any cell culture sample. The nucleic acid samples may also be derived from any molecular biology, microbiology, and/or recombinant DNA techniques known in the art. Prior to examination by the methods described in the present disclosure, the nucleic acid samples may also be amplified and transcribed into RNAs by any technique known in the art, such as but not limited to TMA, sequential utilization of PCR and RNA transcription, or any combinations thereof.

The methods of the present disclosure enable simultaneous detection of the genetic alteration(s) in one or more targets of interest, which may be present in a sample at a very low frequency. For example, mutants may be present among several hundred thousands of non-mutants, in contrast to most mutation detection assays which are limited to detection sensitivities of approximately 1-10%. Moreover, the methods and products of the present disclosure enable simultaneous mutation analysis of a multitude of multiple targets of interest in any one or more samples which may be analyzed simultaneously, sequentially, or any combinations thereof.

Figure 1B:
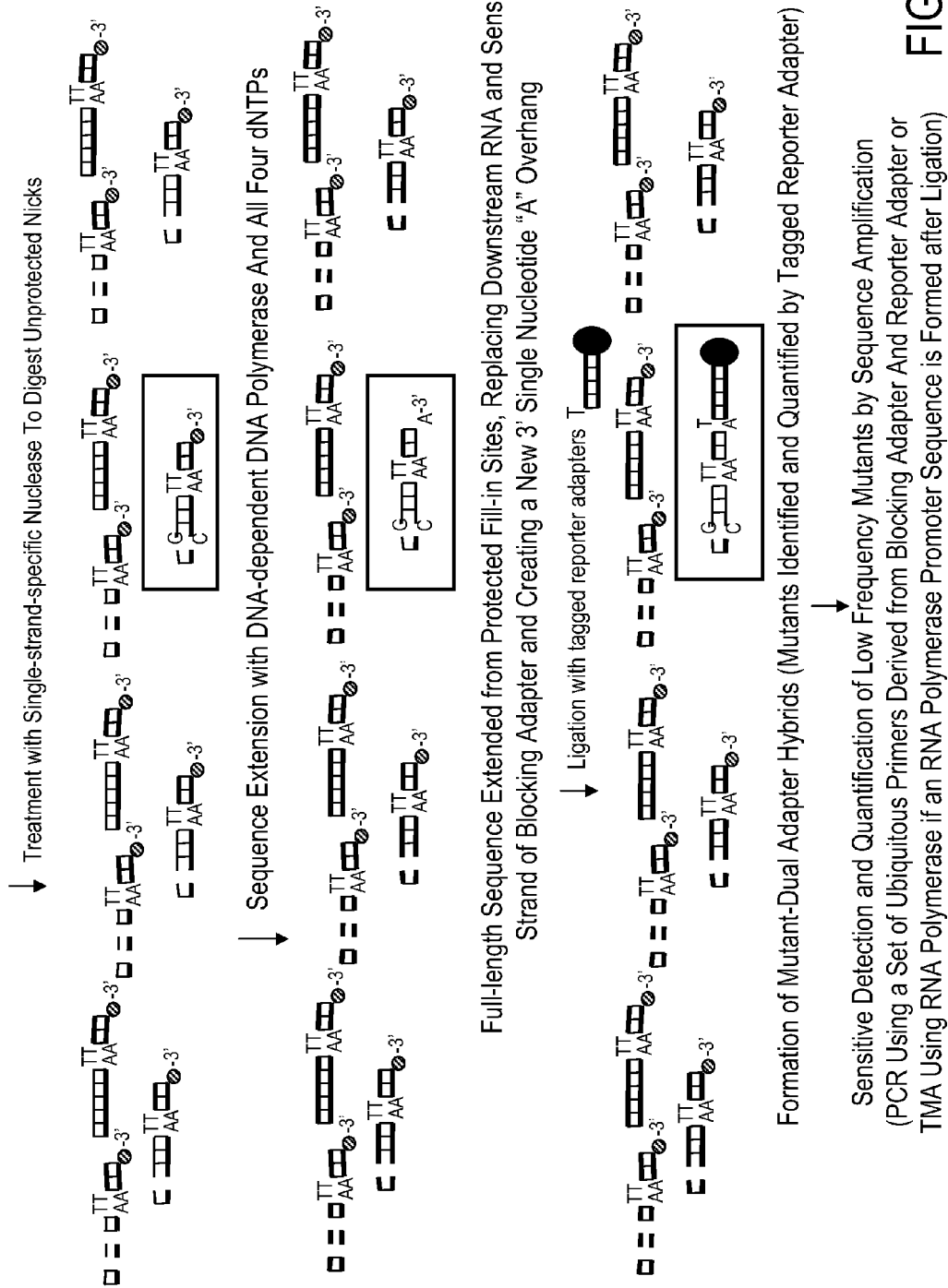

Generally the methods of the present disclosure include a series of molecular reactions as depicted in FIG. 1: (1) harvests of RNAs or transcript amplification from tested samples; (2) synthesis of antisense single-stranded wild-type DNA probes of interest, each carrying at least an extra "deoxy-T" at the 5' end; (3) dividing each tested RNA sample into four (or two) fractions and subjecting each fraction to hybridization with the antisense DNA probes that may be in liquid form or immobilized on solid phase media; (4) subjecting resulting RNA:DNA heteroduplex molecules to ribonuclease digestion; (5) sequence extension from nicked ribonucleotide sites and the 3' end of target RNAs using an RNA-primed DNA polymerase and dATP to create a 3' single nucleotide "deoxy-A" overhang on the sense strand of resulting dATP-modified RNA:DNA heteroduplexes; (6) ligation with a blocking adapter that carries a 3' single nucleotide "deoxy-T" overhang on the antisense strand and dual (5' and 3') phosphorylations on the sense strand; (7) differential sequence fill-in (DSF) by the use of an RNA-primed DNA polymerase and one of four dNTPs (dATP, dCTP, dGTP, and dTTP) respectively in the four fractions of each tested sample (or the use of two dNTPs separately in two different reactions); (8) digestion with a single-strand-specific nuclease to hydrolyze unprotected or partially protected deoxyribonucleotides wherein nicked ribonucleotide sites are not filled in or are partially filled in, in contrast to full protection of single nucleotide nicks that are filled in with a complementary dNTP; (9) full-length sequence extension from fully protected fill-in sites by the use of a DNA-dependent DNA polymerase and all four dNTPs, leading to the displacement of downstream RNA and the sense strand of the blocking adapter, and subsequently the creation of a new single nucleotide "deoxy-A" overhang carrying a free 3'-OH; and (10) ligation with a tagged reporter adapter that carries a 3' single nucleotide "deoxy-T" overhang at its antisense strand to form mutant-dual adapter hybrids for mutation detection and/or quantification. Targeting the tag on the reporter adapter, the detection and/or quantification of mutants may be performed by any signal detection, quantification or enhancement method known in the art. Moreover, for sensitive detection of low frequency mutants, mutant-dual adapter hybrids may be subject to sequence amplification, such as but not limited to the use of PCR, LCR, TMA or any combinations thereof. The formation of mutant-dual adapter hybrids makes it possible to perform PCR using a set of two ubiquitous primers derived respectively from the blocking adapter and the reporter adapter, regardless of the number, the origin, and the location of mutant genes involved. In another non-limiting approach, sequence amplification is carried out by the use of LCR and a set of two ubiquitous adapters to amplify the commonly shared sequence at the crossover site of dual adapter ligation products. Another non-limiting sequence amplification method is the use of TMA. It may be achieved by embedding a T3, T7, or SP6 promoter sequence in the reporter adapter or by designing the blocking adapter and the reporter adapter in such a way that, following the ligation of the reporter adapter to the blocking adapter at the 3' end of mutant targets, a T3, T7, or SP6 promoter sequence is formed. As a result, through the use of corresponding T3, T7, or SP6 RNA polymerase and its substrates, mutant-dual adapter hybrid sequences may be amplified by TMA for sensitive mutation detection and characterization. In another non-limiting approach, a third adapter may be ligated to the 5' end of mutant-dual adapter hybrids to form mutant-triple adapter hybrids. Consequently, mutant sequences are flanked by the third adapter at the 5' end and the dual adapters at the 3' end. Employing PCR using primers derived from the third adapter and the reporter adapter, mutant-triple adapter hybrids are therefore amplified, sequenced, and identified.

Generally the blocking adapter and the reporter adapter in the present disclosure are at least 10 base pairs (bps) in length, preferably at least 12 bps, and may be as large as several thousand bps. In one non-limiting embodiment, the adapters are from about 16 to about 50 bps in length. In one non-limiting embodiment, the blocking adapter has three unique features: (1) a 3' single nucleotide "deoxy-T" overhang on its antisense strand to enable the ligation with the 3' single nucleotide "deoxy-A" overhang of dATP-modified RNA:DNA heteroduplexes of interest; (2) a 5' phosphate on the sense strand that allows the ligation with the free 3'-OH of the 3' "deoxy-A" overhang on dATP-modified RNA:DNA heteroduplexes; and (3) the attachment of a phosphate group or any inert substrate to hinder the 3'-OH on its sense strand and to prevent further ligation with any adapter. The corresponding reporter adapter has a 3' single nucleotide "deoxy-T" overhang on its antisense strand and a 5' phosphate on its sense strand. Moreover, the reporter adapter may be tagged with a detectable marker, molecule or substrate for the detection and/or quantification by any applicable signal detection, quantification or enhancement method known in the art. As used herein a "tag" refers to any atom, molecule, compound or substrate which may be used to confer a detectable and/or quantifiable signal or may be used for signal amplification, and which may be attached to a nucleic acid, peptide, protein, carbohydrate, fatty acid, lipid, glycoprotein, glycolipid, any molecule, any compound or any combinations thereof. Any tag known in the art may be utilized herein including, but not limited to, a fluorescent dye, a colorization agent, a radioactive isotope, a chemiluminescent substrate, an ELISA substrate, a luciferase substrate, a magnetic tag/bead, and any combinations thereof. The tag may be detectable, quantifiable and/or amplifiable by any suitable technique known in the art including, but not limited to, fluorimetry, colorimetry, scintillation counting, autoradiography, ELISA assay, use of any type of camera such as a CCD camera, luminometry, magnetism, enzymatic activity, and any combinations thereof.

As described above, the ligation of the blocking adapter to RNA:DNA heteroduplex molecule is preferably taking advantage of a single nucleotide "deoxy-A" overhang on the sense strand of RNA:DNA heteroduplexes and a single nucleotide "deoxy-T" overhang on the antisense strand of the blocking adapter. However, other non-limiting approaches may also be employed. For example, the antisense wild-type DNA probes may be embedded with at least one extra deoxycytidine (deoxy-C) at their 5' ends and then using dGTP as the sole substrate for sequence extension following ribonuclease digestion of RNA:DNA heteroduplexes to create a single nucleotide "deoxyguanidine (deoxy-G)" overhang. Consequently, by the use of a blocking adapter carrying a single nucleotide "deoxy-C" on its antisense strand, this blocking adapter may be ligated to RNA:DNA heteroduplexes carrying a single nucleotide "deoxy-G" overhang. Likewise, if the antisense DNA probes are embedded with at least one extra "deoxy-A" or "deoxy-G", the substrate used for sequence extension following ribonuclease digestion would be dTTP and dCTP, respectively. And, the single nucleotide overhang on the antisense strand of the blocking adapter would be "deoxy-A" and "deoxy-G", respectively. Moreover, it is also feasible to employ blunt-end ligation by the use of a high concentration of ligase in the ligation reaction. In such case, there would be no need for embedding extra deoxyribonucleotides at the 5' end of the antisense DNA probes. Following ribonuclease digestion on RNA:DNA heteroduplexes of interest, a blunt-ended blocking adapter may be ligated without the need of performing RNA-primed DNA sequence extension for the creation of a sticky end. Taken together as a general rule, the ligation of the blocking adapter to RNA:DNA heteroduplexes of interest may be carried out through a compatible sticky end or through blunt-end ligation by any nucleotide linkage method known in the art, such as but not limited to an enzymatic reaction, a chemical reaction, a physical reaction or any combinations thereof.

DSF reactions and subsequent single-strand-specific nuclease digestion result in four possible products: (1) fully protected wild-type heteroduplex-blocking adapter hybrids; (2) fully protected mutant heteroduplexes as a result of complete fill-in with a complementary dNTP at single nucleotide nicks; (3) hydrolysis of unprotected deoxyribonucleotides at single nucleotide nicks in mutant heteroduplexes that are not filled in due to the use of a non-complementary dNTP, and (4) digestion of multinucleotide nicks in homologous heteroduplexes that are partially filled in. As a result, those unprotected or partially protected products become fragmented after single-strand-specific nuclease digests. In contrast, mutants with a single nucleotide nick filled in by a complementary dNTP may subsequently undergo full-length sequence extension, leading to the displacement of the sense strand of the blocking adapter, creation of a new 3' single nucleotide "deoxy-A" overhang, and enabling the ligation with a tagged reporter adapter to form mutant-dual adapter hybrids. Although wild-type heteroduplexes are fully protected from single-strand-specific nuclease digestion, there are no ribonucleotide nicks and no deoxyribonucleotide fill-ins to initiate new sequence extension. Therefore, wild-type heteroduplexes remain blocked by the blocking adapter and are unable to form dual adapter ligation products. By targeting the tag of the reporter adapter or mutant-dual adapter hybrids, mutants may then be detected and/or quantified.

There are two key purposes for sequentially utilizing DSF, single-strand-specific nuclease digestion and full length sequence extension with all four dNTPs in the present disclosure: (1) to avoid false positives that may result from sequence homologues and (2) to avoid multiple target-specific amplifications that are needed in current mutation detection assays in order to analyze multiple different target genes of interest. Likewise, the purposes of employing sequential ligation of a blocking adapter with a reporter adapter in the present disclosure are (1) to assure the specificity of mutation detection and (2) to universalize the sequence amplification step for mutants of all different origins. Nonetheless, modifications may be made to devise alternative approaches that employ the principle of DSF reactions without the use of a blocking adapter. As a result, mutant-reporter adapter hybrids are thus formed instead of the formation of mutant-dual adapter hybrids. In a non-limiting embodiment, mutation detection assays may be carried out without the use of a blocking adapter as demonstrated by the following: (1) hybridization of RNA samples with antisense DNA probes to form RNA:DNA heteroduplexes, (2) ribonuclease digestion to nick mismatched ribonucleotides, (3) dividing samples into four (or two fractions) and performing DSF respectively with each of four dNTPs (or with two dNTPs in one fraction and the other two dNTPs in the other fraction), (4) treatment with a single-strand-specific nuclease to digest partially filled heteroduplexes, (5) sequence extension with all four dNTPs to create a 3' single nucleotide "deoxy-A" on mutant heteroduplexes filled in with a complementary dNTP, (6) ligation with a tagged reporter adapter carrying a 3' single nucleotide "deoxy-T" on the antisense strand, (7) mutation detection and signal enhancement by targeting the tag of the reporter adapter or by sequence amplification of the resulting mutant-reporter adapter hybrids. Of note is that the ligation of the reporter adapter to mutant RNA:DNA heteroduplexes may also be accomplished through the sticky end of a restriction enzyme (RES). In such case, an "RES" sequence is embedded at the 5' end of the antisense DNA probes. As a result of full-length sequence extension in mutant heteroduplexes filled in with a complementary dNTP, a corresponding "RES" site is formed. Following digestion with the corresponding "RES", a sticky end of this "RES" is formed, thereby enabling the ligation with a tagged reporter adapter that carries a compatible sticky end. The mutation detection or amplification may then be directed to the tag of the reporter adapter or the resulting mutant-reporter adapter hybrids. In a non-limiting approach for sequence amplification of the resulting mutant-reporter adapter hybrids, a T3, T7 or SP6 promoter sequence is embedded in the reporter adapter. By the use of the corresponding RNA polymerase and its substrates, mutant-reporter adapter hybrids are therefore amplified and identified. In another non-limiting approach, a stretch of known sequence, such as but not limited to a T3, T7 or SP6 promoter sequence or an M13 sequence, is embedded at the 3' end of the antisense DNA probes. Prior to single-strand-specific nuclease digestion, the embedded sequence on the antisense DNA probes is protected by incubating RNA:DNA heteroduplexes with a complementary oligonucleotide. Following full-length sequence extension and ligation with a reporter adapter, the resulting mutant-reporter adapter hybrids of all different origins would share the same flanking sequences: a T3, T7, SP6 promoter sequence or an M13 sequence at one end and a reporter adapter sequence at the other end. Consequently, PCR may be performed by the use of two ubiquitous primers to amplify the mutant-reporter adapter hybrids.

As described above, if the ligation of a blocking adapter to RNA:DNA heteroduplexes is to take advantage of a compatible A/T sticky end, the single-stranded antisense DNA probes in the present disclosure are preferably embedded with at least one extra "deoxy-T" at the 5' end. The antisense probes may be synthesized by any method known in the art to be useful for producing single-stranded antisense DNA. In one non-limiting embodiment, a sample of normal RNA is used as a template for reverse transcription (RT)-mediated PCR to amplify cDNA fragments of target genes. The resulting cDNA fragments may then be used as templates to synthesize antisense single-stranded DNA probes by performing PCR with a corresponding reverse primer that carries at least one extra deoxyribonucleotide (preferably an extra "deoxy-T") at its 5' end. In another non-limiting embodiment, RT-mediated PCR is performed by the use of a forward primer and a reverse primer that flank a target genetic region of interest. Of note is that the reverse primer carries at least an extra "deoxy-T" and a biotin molecule at its 5' end. Consequently, the resulting PCR amplified cDNA fragments of target genes carry at least an extra "deoxy-T" and a biotin molecule at the 5' end of their antisense strands. Moreover, the biotin molecule on the antisense strands make it possible to immobilize biotinylated antisense strands firmly onto a streptavidin-coated solid phase media through a covalent bond, leaving unbiotinylated sense strands unbound and easily removed after denaturation and washing. The immobilized antisense single-stranded DNA may then be used as the probes for the mutation detection methods described in the present disclosure. Probes used in the present disclosure may be in the range of about 20 nucleotides to several kilobases, preferably in the range of about 50 to about 1000 nucleotides.

The hybridization reaction carried out to create RNA:DNA heteroduplex molecules utilized in the present disclosure may comprise any one or more antisense DNA probes, wherein each probe is specific for a different genetic region of interest. For example, probe A is specific for gene A, probe B is specific for gene B, and probe C is specific for gene C, etc. The hybridization reaction may comprise any one or more species of transcript, i.e. transcript A of gene A, transcript B of gene B, transcript C of gene C, etc. Thus, resulting RNA:DNA heteroduplex molecules may comprise more than one species/population of RNA:DNA heteroduplexes, i.e. heteroduplex A, heteroduplex B, heteroduplex C, etc. Any one or more of these species of heteroduplexes may contain one or more mutant members, i.e. mutant A, mutant B, mutant C, etc. It is also possible that more than one mutation is present and detected in any type/species of heteroduplexes. For example, mutant A1 contains mutation 1, mutant A2 contains mutation 2, and mutant A3 contains mutation 3 in heteroduplex A. Each different mutation may be represented and populated by any individual member.

Figure 2:
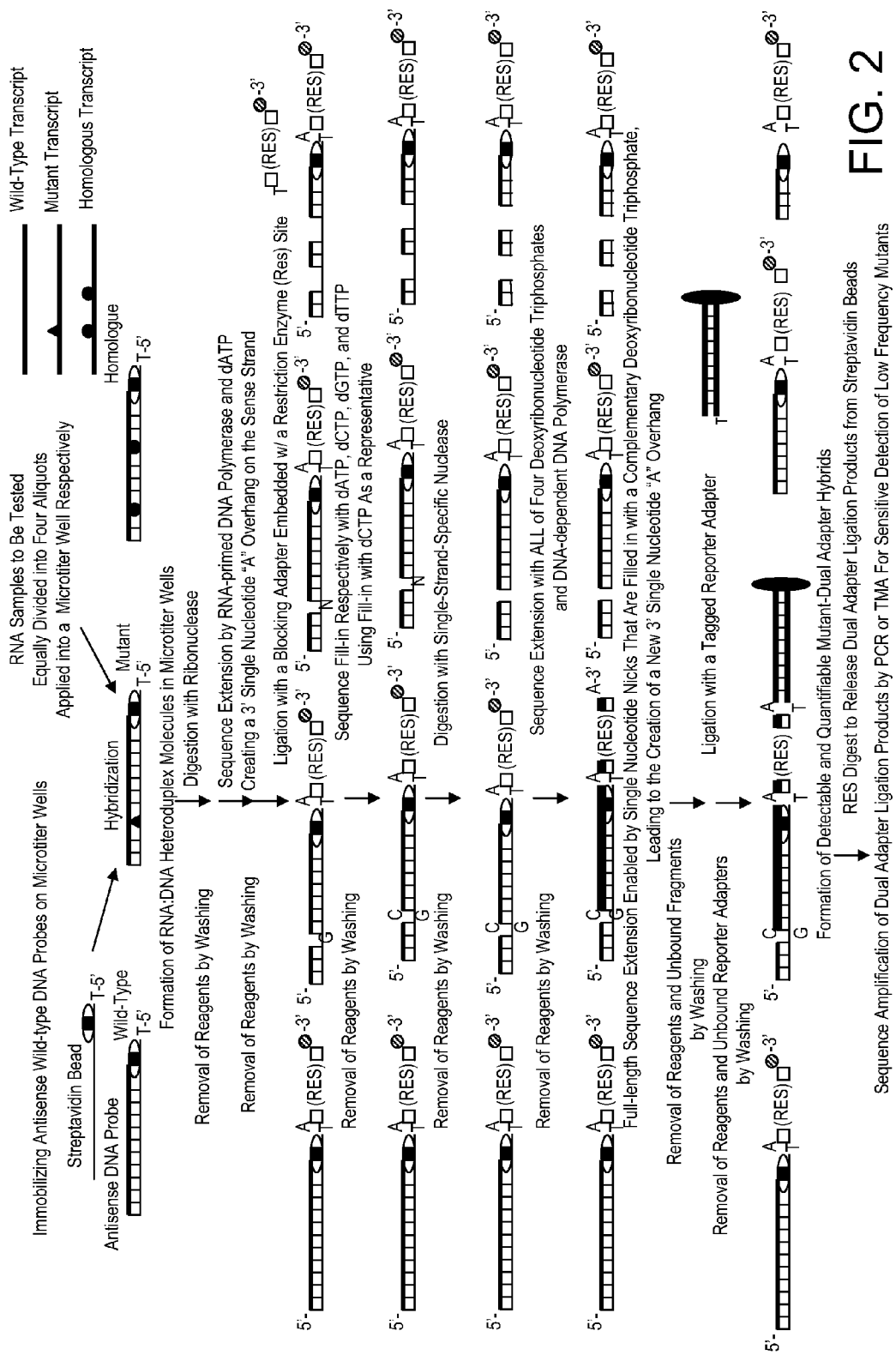
FIG. 2 provides an overview of a non-limiting method that employs a streptavidin-based solid phase media to facilitate the conduction of a series of molecular reactions described in the present disclosure for the detection of low frequency mutants.

The mutation detection methods of the present disclosure comprise a series of different molecular reactions, wherein each reaction comprises different reaction products and/or reagents. The products and/or reagents of one step may interfere with the subsequent reaction(s). During the development and optimization of the methods of the present disclosure, it has been discovered that these molecular reactions may be performed easily on solid phase media wherein the antisense DNA probes or RNA samples are immobilized. As a result, a series of different reactions may be carried out sequentially in the same vessel with the simplicity of washing followed by the application of appropriate reagents and incubation at an optimized condition. A multitude of multiple different DNA probes may be immobilized in a vessel wherein a tested sample is applied. Performing these molecular reactions in a carrier that accommodates a multitude of multiple different vessels permits simultaneous examination of a multitude of multiple different samples. As a result, a multitude of multiple different targets of interest may be analyzed simultaneously in a multitude of multiple different samples. In a non-limiting embodiment as depicted in FIG. 2, a multitude of multiple different biotinylated antisense DNA probes are mixed and immobilized in each well of a streptavidin-coated 96-well microtiter plate. Each tested RNA sample may be equally divided into four fractions, applied separately to a well in the 96-well plate, and labeled as "A," "C," "G," and "T," respectively. DSF reactions using dATP are performed in wells labeled as "A." DSF reactions using dCTP are performed in wells labeled as "C." DSF reactions using dGTP are performed in wells labeled as "G." DSF reactions using dTTP are performed in wells labeled as "T." As a result, the 96-well plate may accommodate 24 different RNA samples, each having four different DSF reactions. As depicted in FIG. 2, a series of molecular reactions are sequentially carried out by the use of appropriate reagents and incubation in an optimized condition after washing in an automated microtiter plate washer. Consequently, a series of different molecular reactions from the initial probe hybridization to the final step of reporter adapter ligation are completed in the streptavidin-coated microtiter plate for simultaneous examination of a multitude of multiple different targets of interest in 24 samples with minimal hands-on time and effort. The number of tested samples may be increased to 48 if DSF reactions are performed in pairs, i.e., using two dNTPs in one well and the other two dNTPs in another well. The number of tested RNA samples may be increased to 192 with the use of a 384-well plate. The capacity may be increased further by the use of an automated microtiter plate washer that accommodates multiple plates simultaneously. Following the ligation with a tagged reporter adapter, wells harboring mutants filled in with a complementary dNTP may be detected and/or quantified by any applicable signal detection, quantification or enhancement method known in the art. Mutation detection and/or quantification may also be carried out by targeting mutant-dual adapter ligation products. In a non-limiting approach as depicted in FIG. 2, the blocking adapter carries an embedded restriction enzyme (RES) site. Therefore, the mutant-dual adapter ligation products may be released from solid phase media by "RES" digestion. With subjection to sequence amplification by PCR, LCR or TMA, even a small amount of mutant-dual adapter ligation products may be amplified and sensitively detected and/or quantified. In addition to "RES" digest, mutant-dual adapter ligation products may be released from solid phase media by any method known in the art, such as but not limited to denaturation by heat or alkaline treatment.

As depicted in FIG. 3, there is provided a non-limiting method to perform mutation detection on solid phase media in microarray format. Herein solid phase media refer to any material known in the art including but not limited to a slide, a film, or a membrane that permits the immobilization of single-stranded DNA probes in microarray format. A holder device that holds the solid phase media may be employed to facilitate the conduction of a series of different molecular reactions described above. Of note is that the holder device may be adapted for use in an automated microtiter plate washer. In a non-limiting embodiment, this holder device holds six standard microscopy slides and transforms into a standard 96-well plate upon assembly. As depicted in FIG. 3, a multitude of hundreds of different antisense DNA probes may be immobilized in array format in each well, wherein each probe is spotted at a specific location numbered respectively as position "1" through position "N" and each probe is spotted in duplicates and labeled respectively as "A" and "B." At least 24 RNA samples may be tested in this holder device. RNA samples may be harvested from tested samples or synthesized by any method known in the art that permits transcript amplification of target genes of interest from tested samples, such as but not limited to TMA or the use of PCR amplification followed by RNA transcription. Each of the RNA samples to be tested is equally divided into four fractions, and each fraction is subjected to DSF respectively with each of four dNTPs in a well of the holder device. As described above, a series of molecular reactions may be carried out sequentially in the holder device through the application of appropriate reagents and incubation in an optimized condition followed by washing in an automated microtiter plate washer. After the ligation with a tagged reporter adapter, the slide or membrane may be detached from the holder device and then subjected to signal analysis by any applicable detection method or signal enhancement method known in the art that targets the tag of the reporter adapter or mutant-dual adapter hybrids. As depicted in FIG. 3, detectable signals are present at positions A1(B1), A3(B3), A4(B4) in a well harboring mutants that are filled in with a complementary dNTP and undergo full-length sequence extension. Because the specific location of each probe is known, spots harboring detectable signals lead to immediate identification of mutant genes involved. The number of tested samples may be doubled to 48 if DSF reactions are performed with two dNTPs in a well and the other two dNTPs in another well. The capacity may be increased to 192 samples through the use of a holder device that transforms into a 384-well plate. The number of tested samples may be increased further by the use of an automated microtiter plate washer that accommodates multiple plates.

Figure 4:
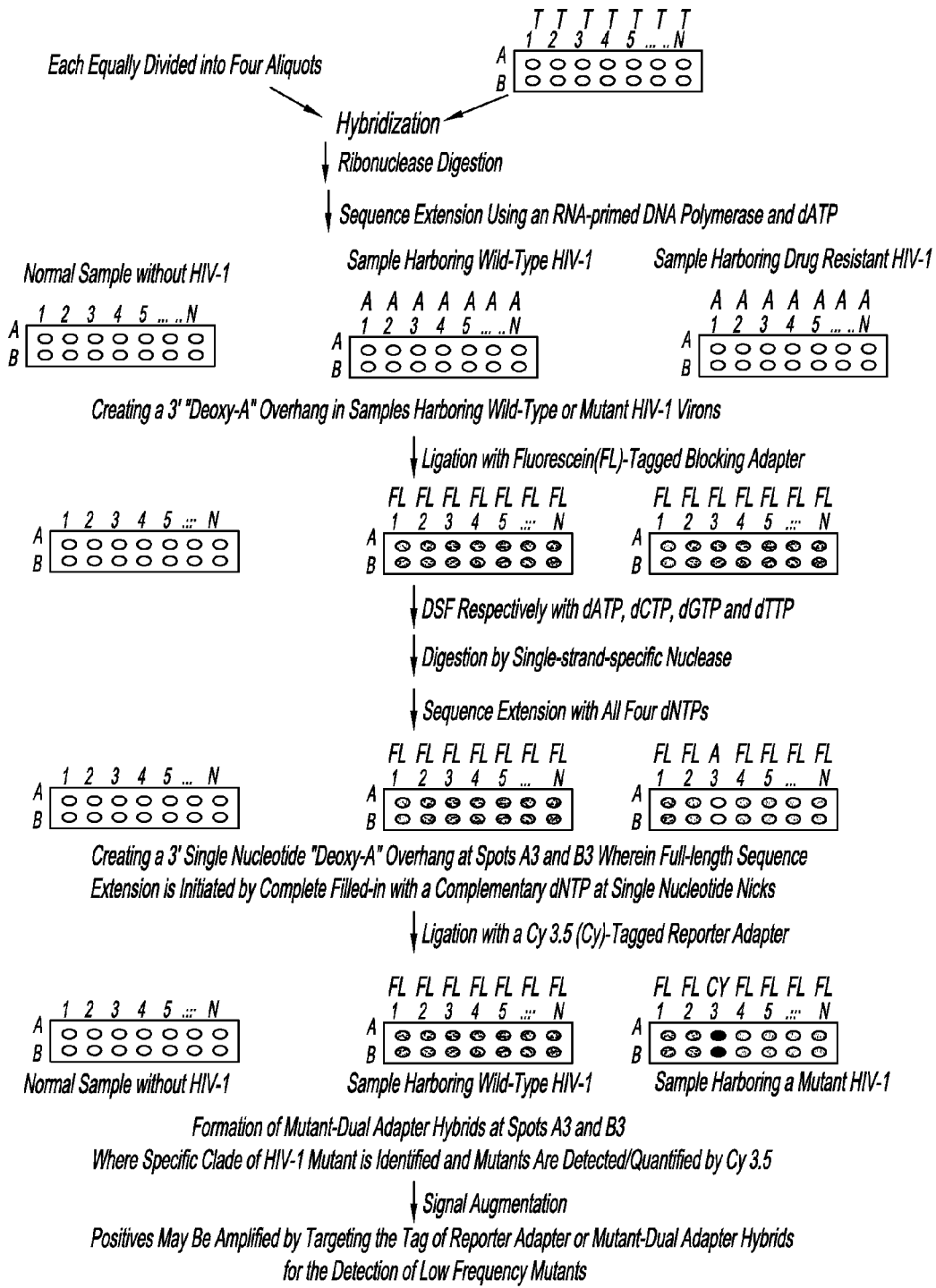
FIG. 4 provides an overview of a non-limiting method for detecting type 1 human immunodeficiency virus (HIV-1) and mutations in the pol gene of various HIV-1 clades in array format.

Referring now to FIG. 4, there is provided an overview of a non-limiting method for the detection of an infectious microorganism and drug resistant mutants, such as but not limited to HIV-1 and drug-resistant mutants. As depicted in FIG. 4, antisense DNA probes specific for the pol gene of each different clade of HIV-1 are immobilized separately in array format on a solid phase media. The probes are numbered and arrayed in duplicates. Raw "A" and Raw "B" are identical. As described above, each antisense DNA probe carries at least one extra "deoxy-T" at its 5' end. Viral RNAs are harvested and may be amplified from tested samples by any method known in the art, such as but not limited to TMA or RNA transcription of PCR amplified HIV-1 pol cDNAs. RNA samples are then divided into four aliquots and subjected to hybridization with the antisense DNA probes. Following the formation of RNA:DNA heteroduplex molecules, a series of molecular reactions are carried out on solid phase media, including ribonuclease digestion, sequence extension with an RNA-primed DNA polymerase and dATP, ligation with a tagged blocking adapter, DSF respectively with each of four different dNTPs, digestion with a single-strand-specific nuclease, sequence extension using a DNA-dependent DNA polymerase and all four dNTPs, and ligation with a tagged reporter adapter. Of note is that the blocking adapter may be tagged with any detectable marker known in the art, such as but not limited to a fluorescent dye, Fluorescein (FL), and the reporter adapter may be tagged with another detectable marker, such as but not limited to another fluorescent dye, Cy3.5 (Cy). As depicted in the left panel of FIG. 4, normal samples without HIV-1 virons have no detectable fluorescence following the ligation with the FL-tagged blocking adapter due to the absence of HIV-1 RNAs to form RNA:DNA heteroduplexes. On the other hand, samples harboring wild-type HIV-1 or drug resistant mutants are first stained by the FL-labeled blocking adapter. As depicted in the right lower panel of FIG. 4, further manipulations result in full-length sequence extension and ligation with the Cy-tagged reporter adapter at spots A3 and B3 wherein drug resistant mutants are filled in with a complementary dNTP and fully protected from single-strand-specific nuclease digest. In contrast, due to the absence of full-length sequence extension, the FL-tagged blocking adapters are retained at spots occupied by wild-type HIV's of same clade (the middle panel of FIG. 4), wild-type HIV's of different clade, and mutants that are not filled in with a complementary dNTP.

Referring now to FIG. 5, there is provided an overview of a non-limiting method for rapid screening and sensitive detection for the presence of an infectious microorganism and mutants, such as but not limited to HIV-1 and drug resistant mutants. In a non-limiting embodiment as depicted in FIG. 5, a mixture of biotinylated antisense wild-type DNA probes specific for different clade of the HIV-1 pol gene are immobilized in each well of a streptavidin-coated microtiter plate. Viral RNAs are harvested from tested samples. To increase the assay sensitivity, viral RNAs may be subject to transcript amplification by any method known in the art that is applicable to the amplification of target RNAs. Each tested RNA sample is divided into 4 aliquots and applied separately to a well of the streptavidin-coated microtiter plate. A series of molecular reactions, starting from probe hybridization to ligation with a reporter adapter, are carried out sequentially by the application of appropriate reagents, incubation in an optimized condition, and followed by washing in an automated microtiter plate washer. Of note is that the blocking adapter carries a restriction enzyme (RES) site and the reporter adapter is tagged with a detectable marker. As depicted in the left panel of FIG. 5, there is no adapter present in wells wherein HIV-1 virons are absent. As depicted in the middle two panels of FIG. 5, the blocking adapter is attached in wells harboring wild-type HIV-1 virons of the same clade or different clade. Mutants that are not filled in with a complementary dNTP are also blocked by said blocking adapter (not shown). In contrast, as depicted in the right panel of FIG. 5, mutants that are filled in with a complementary dNTP undergo full-length sequence extension and permit the ligation of the tagged reporter adapter to the blocking adapter. As a result, by targeting the tag of the reporter adapter, any applicable signal detection/quantification or enhancement method may be employed to identify samples harboring HIV-1 mutants that are filled in with a complementary dNTP. Moreover, by taking advantage of the "RES' site embedded in the blocking adapter, digestion with the corresponding 'RES" enzyme releases dual adapter ligation products which may then be amplified by PCR using a set of two ubiquitous primers to detect small amounts of HIV-1 mutants sensitively. Alternatively, as described above, LCR or TMA may be employed to amplify and detect low frequency mutants.

There is also provided an overview of a non-limiting method for detecting a mutation or mutations residing within a multitude of multiple different genes in tissue sections or cell preparations that are fixed onto a solid phase media, such as but not limited to a microscopy slide or a film. This non-limiting approach permits simultaneous examination of a multitude of multiple different genetic mutations while preserving cell morphologies for microscopic examination. The general method is similar to that described for FIG. 3 and FIG. 4 except that tested cellular RNA samples are immobilized on a slide or any solid phase media known in the art. A set of four slides is subject to examination. If target transcripts are in low abundance, after immobilizing cellular nucleic acid contents, any transcript amplification method known in the art may be performed in situ to enhance the assay sensitivity. After rehydration, the tissue sections or cell preparations are subject to hybridization with a mixture of antisense wild-type DNA probes that target a multitude of multiple different genetic regions of interest. As described above, each of the antisense probes carries at least an extra "deoxy-T" at its 5' end. After the formation of RNA:DNA heteroduplexes on the solid phase media, a series of molecular reactions are carried out, including ribonuclease digestion, sequence extension by an RNA-primed DNA polymerase and dATP, ligation with a blocking adapter, DSF respectively with each of four dNTPs on each slide (or two dNTPs on one slide and the other two dNTPs on another slide), digestion with a single-strand-specific nuclease, sequence extension using a DNA-dependent DNA polymerase and all four dNTPs, and subsequent ligation with a tagged reporter adapter. As explained above, only cells harboring mutant targets that are filled in with a complementary dNTP and undergo full-length sequence extension would permit the ligation with the tagged reporter adapter. By targeting the detectable tag on the reporter adapter, any applicable signal detection or enhancement method may be employed to identify mutants. For example, if the tag on the reporter adapter is a fluorescent dye, mutants may be identified by a fluorescent microscope or a fluorescent CCD camera. In another non-limiting example, the tag on the reporter contains a colorable substrate for signal enhancement. As a result, mutants may be identified under a light microscope.

Other non-limiting embodiments of the present disclosure are directed to products that facilitate the execution of the mutation detection methods of the present disclosure. In one non-limiting embodiment, there is provided a kit (or kits) comprising reagents and a user's guide providing instructions for performing a method (or methods) of the present disclosure. The user's guide may comprise hardcopy printed literature, computer readable media, and any combinations thereof. The kit(s) may be custom-made for analysis of any one or more genetic targets of interest; or the kit(s) may comprise key reagents and materials for broad range mutational screening applications that are based on the methods of the present disclosure; or the kit(s) may comprise all or some of reagents and materials that employ the methods of the present disclosure to detect any of a number of mutations commonly associated with and/or observed in any one or more medical condition or disease, such as a cancer, a hereditary disorder, an infectious microorganism, a cellular function, or a cellular function pathway, etc. Generally the reagents and materials of the kit(s) include probes necessary to screen genetic regions of interest. The probes may be synthesized as described above in the disclosure. The probes may be provided individually or a mixture of different probes may be provided in solution or in lyophilized powder form, or a multitude of multiple different probes may be attached on a solid phase media as was described elsewhere in the present disclosure. In one non-limiting embodiment, probes provided are coupled with a molecule or a tag for immobilization onto a solid phase media, and they are suspended in an appropriate buffer solution or present in lyophilized form. In another non-limiting embodiment, probes are provided in array format on a solid phase media, such as deposition in any array on one or more microtiter plates, on a membrane, on a slide or as a DNA microarray/chip. Any method known in the art for producing DNA arrays may be used to create DNA microarrays of the present disclosure. In another non-limiting embodiment, probes are mixed and immobilized onto each well of a microtiter plate. Any RNA samples may be assayed with the kit(s) of the disclosure provided. RNA transcripts may be prepared or amplified as detailed previously in the disclosure. Generally the kit(s) may be targeting a certain molecular biological function, pathway or marker, such as but not limited to: 1) a kit specific for screening for mutation in oncogenes and comprising probes specific for known oncogenes; (2) a kit specific for screening mutation in tumor suppressor genes and comprising probes specific for known tumor suppressor genes; (3) a kit specific for screening for mutation in mismatch repair genes and comprising probes specific for mismatch repair genes; (4) a kit specific for screening for mutation in tyrosine kinase genes also called "Tyrosine Kinome" and comprising probes specific for tyrosine kinase genes; (5) a kit specific for screening for mutation in growth factor receptor genes and comprising probes specific for growth factor receptor genes; (6) a kit specific for screening for mutation in mitochondrial DNA, either within D-loop or non-D-loop (coding) regions and comprising probes specific to those regions; (7) a kit specific for screening miRNAs and comprising probes specific for miRNAs; (8) a kit specific for screening SNP markers and comprising probes specific for SNP markers; (9) a kit specific for screening microsatellite polymorphism markers and comprising probes specific for microsatellite polymorphism markers; and (10) a kit specific for screening for the presence of infectious microorganisms and mutants and comprising probes specific for target microorganisms of interest. The kit(s) may also be targeting a disease by including a selected combination of different probes for genetic regions frequently associated with mutations in diseases of interest, such as but not limited to a kit for breast cancer, a kit for colon cancer, a kit for prostate cancer, and a kit for lung cancer, etc. The kit(s) may also include a selected combination of different probes to target a stage of a disease, subtypes of a disease, or a clinical status, such as but not limited to carcinoma in situ of breast cancer, infiltrating ductal carcinoma of breast cancer, metastatic breast cancer, or resistance to a specific type of treatment.

In addition to user's guide and probes, the kit(s) may further comprise all or some of the reagents that are needed to carry out a series of molecular reactions described above. The kit(s) may include a set of blocking adapter and reporter adapter described above. The kit(s) may also include reagents for RNA extraction, PCR or TMA for preparation and amplification of RNA transcripts to be used in hybridization with the probes provided in the kit(s) to create RNA:DNA heteroduplexes according to the instructions in the user guide. The kit(s) may also be designed to include reagents and primers that permit PCR, real-time PCR, LCR or TMA amplification of mutant-dual adapter hybrid products and/or mutant-triple adapter products described above. The kit(s) may also include reagents for signal detection/quantification and/or enhancement of said reporter adapter and/or said blocking adapter provided in the kits. The kit(s) may also include reagents and primers to carry out DNA or RNA sequencing of mutant-dual adapter hybrids and/or mutant-triple adapter hybrids.

Unless stated otherwise, the practice of the present disclosure makes use of molecular biology, microbiology and recombinant DNA techniques. All general and support techniques utilized and applicable herein are explained fully in the literature. The reagents and machinery for PCR, real-time PCR, LCR, TMA, probe hybridization, nuclease digestions including but not limited to ribonuclease, single-strand-specific nuclease, restriction enzyme, DNA and RNA polymerase reactions, ligations, amplification of transcripts, detection/quantification methods, and all other molecular biology techniques and recombinant DNA techniques are known by one of skill in the art and are suitable for use herein. Simple adjustments made to known reaction variables, such as reaction temperature and duration, reagent concentration, the design of oligonucleotides for PCR or LCR, and the design of adapters whether tagged or untagged, should not be misconstrued as undue experimentation but rather understood to be within the skill of one in the art.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, and/or use of equivalent functional reactions for reactions described herein. Any insubstantial variations are to be considered within the scope of the claims below.

EXAMPLE

A Streptavidin-Captured Mutation Assay for Simultaneous Analysis of Multiple Different Genes by DSF-Enabled Sequential Adapter Ligation and Amplification The present example illustrates one non-limiting application of the present disclosure for simultaneous screening of a multitude of multiple different genes for the presence of a mutation or mutations by the use of a streptavidin-coated microtiter plate. RNA samples are harvested from eight normal blood samples as negative controls and ten neoplastic cell lines of various origin: NCI-H460 lung cancer cells, HCT-15 colon cancer cells, SW-480 colon cancer cells, MCF7 breast cancer cells, KG-1 myeloid leukemia cells, HL-60 myeloid leukemia cells, KBM7 myeloid leukemia cells, B15 lymphoblastic leukemia cells, HUT-78 T-cell leukemia cells, and Ryan B-cell lymphoma cells. Targets of interest are the mutation predilection regions of nine different genes: K-ras, TP53, Erb-b2, VEGFR3, MSH6, CHEK2, BRIP1, LKB1, and PIK3CA. This streptavidin-captured mutation screening assay is carried out as the following:

Preparation and Immobilization of Biotinylated Antisense Single-Stranded Wild-Type DNA Probes in a Streptavidin-Coated Microtiter Plate A normal RNA sample is reverse-transcribed and amplified by PCR using a panel of primer sets listed in Table 1. Each set of primers comprises a forward primer and a reverse primer that flank the mutation hot spots of a target gene of interest. Of note is that each of these reverse primers is biotinylated and embedded with two extra "deoxy-Ts" at its 5' end. Consequently, the resulting PCR amplified cDNA fragments carry a biotin molecule and two extra "deoxy-Ts" at the 5' end of their antisense strands.

TABLE 1

Sequences of Nine Sets of Primers Employed to Synthesize Biotinylated cDNA Probes for Nine Target Genes of Interest

| | |
|---|---|
| K-Ras (+) | 5'-GGCCTGCTGAAAATGACTGA-3' |
| K-Ras (−) | 5'-[Biotin]TTCTCCCCAGTCCTCATGT-3' |
| TP53 (+) | 5'-GTCTGGGCTTCTTGCATTGT-3' |
| TP53 (−) | 5'-[Biotin]TTCCCTTCTGTCTTGAACATGA-3' |
| Erb-b2 (+) | 5'-TGGGATCCTCATCAAGCGAC-3' |
| Erb-b2 (−) | 5'-[Biotin]TTGTCATCAGCTCCCACACAGT-3' |
| VEGFR3 (+) | 5'-GAGCAATGCGAATACCTGTC-3' |
| VEGFR3 (−) | 5'-[Biotin]TTCCAGCAGTTCAGCATGATGC-3' |
| MSH6 (+) | 5'-TTAGGACTCTAGTGGCACAC-3' |
| MSH6 (−) | 5'-[Biotin]TTCAGGAAAACGACCTTCAGG-3' |
| CHEK2 (+) | 5'-CTGACTGTAGATGATCAGTC-3' |
| CHEK2 (−) | 5'-[Biotin]TTGGTAGAGCTGTGGATTCATT-3' |
| BRIP1 (+) | 5'-AGCTTACCCGTCACAGCTTG-3' |
| BRIP1 (−) | 5'-[Biotin]TTGTCTGTAATGTGTGCTGATC-3' |
| LKB1 (+) | 5'-TATGGACACGTTCATCCA-3' |
| LKB1 (−) | 5'-[Biotin]TTGTCCTGAGTGTAGATGATGTC-3' |
| PIK3CA (+) | 5'-AATTGGAGATCGTCACAA-3' |
| PIK3CA (−) | 5'-[Biotin]TTTCGGTCTTTGCCTGCTGAGA-3' |

Following PCR amplification, these nine biotinylated PCR products are mixed in a cocktail at a final concentration of one nanogram (ng) per microliter (μl) for each and then denatured in 0.1 M NaOH at room temperature for 5 minutes. The denatured biotinylated PCR products (30 μl) are then applied to each well of a streptavidin-coated 96-well plate, incubated at room temperature for 20 minutes, and then extensively washed in an automated microtiter plate washer. As a result, the biotinylated antisense strands are firmly attached to the wells through covalent bonding in the streptavidin-coated plate while the sense strands are unbound and removed due to the absence of a biotin molecule.

Probe Hybridization, RNase Digestion and Sequence Extension Using dATP

From each of the tested RNA samples, two aliquots (one microgram each) are obtained and labeled as "GA" and "TC," respectively. Each aliquot is subject to hybridization at 45° C. for 1 hour respectively in a well containing 50 μl of 10 mM Tris pH 7.5, 1.25 M NaCl, 30% formamide, and aforementioned nine immobilized antisense wild-type DNA probes in the streptavidin-coated microtiter plate. After hybridization and the formation of RNA:DNA heteroduplex molecules, the microtiter plate is washed in an automated plate washer, and each well is then treated with 20 units of RNase ONE (Promega, Madison, Wis.) in an optimized buffer at 37° C. for 1 hour. After washing in the automated plate washer, sequence extension using dATP is performed at 37° C. for 30 minutes in a reaction buffer (50 µl) containing 5 units of Klenow enzyme, 50 mM NaCl, 5 mM MgCl2, 200 µM of dATP, and 5 mM DTT. As a result, a 3' single nucleotide "deoxy-A" overhang is created on the sense strand of the resulting dATP-modified RNA:DNA heteroduplexes.

Preparation of a Blocking Adapter and Ligation of dATP-Modified RNA:DNA Heteroduplexes with the Blocking Adapter BAdp-Pst(+) 5'-[Phos]CCTGCAGGAGACGGTGA[Phos]-3' and BAdp-Pst(−) 5'-TCACCGTCTCCTGCAGGT-3', two complementary oligonucleotides, are annealed in equimolar concentrations of 10 ng/µl in a buffer containing 50 mM NaCl and 10 mM Tris, pH 8.3 at 65° C. for 15 minutes. BAdp-Pst(+) is phosphorylated at its 5' and 3' ends. BAdp-Pst(−) has an extra "deoxy-T" at its 3' end. As highlighted by underlines, both BAdp-Pst(+) and BAdp-Pst(−) have an embedded Pst-1 restriction enzyme sequence, CTGCAG. Consequently, the resulting double-stranded blocking adapter has a 5' phosphate group and a 3' phosphate group on its sense strand, a 3' "deoxy-T" overhang on its antisense strand, and a Pst-1 site. Due to the presence of 5' phosphate on the sense strand and 3' "deoxy-T" overhang on the antisense strand, this blocking adapter permits the ligation with the 3' "deoxy-A" protruding end on the sense strand of the dATP-modified RNA:DNA heteroduplexes. This ligation reaction is carried out at room temperature for 1 hour in an optimized buffer (50 µl) containing 400 units of T4 DNA ligase and 10 ng of the blocking adapter. Due to the lack of 3'-OH group on the sense strand of the blocking adapter, the resulting RNA:DNA heteroduplex-blocking adapter hybrids are inert for further ligation.

DSF, S1 Nuclease Treatment and Sequence Extension Using All Four dNTPs

For each tested RNA sample, two different DSF reactions are performed and labeled as "GA" and "TC," respectively. In wells labeled as "GA," DSF is performed at room temperature for 45 minutes in an optimized buffer (50 µl) containing 200 µM of dGTP, 200 µM of dATP, 5 units of klenow enzyme, 50 mM of NaCl, 5 mM MgCl2, 5 mM DTT, and 10 mM of Tris pH 7.5. Likewise, DSF using dTTP and dCTP is carried out in wells labeled as "TC." After DSF and washing, samples are subject to S1 nuclease treatment to digest unprotected deoxyribonucleotides at 37° C. overnight in an optimized buffer (50 µl) containing S1 nuclease at the final concentration of 10 units/µl, After washing, unbound and fragmented nucleic acids are removed. Sequence extension using all four dNTPs is then performed at 60° C. for 20 minutes in an optimized buffer (50 µl per well) containing 5 units of Taq DNA polymerase, 10 mM of Tris pH 8.3, 50 mM of KCl, 2.5 mM MgCl2, and 200 µM of each of four dNTPs. As a result of full-length sequence extension that starts from the complete fill-in site and displaces its downstream RNA and the sense strand of said blocking adapter, a new 3' single nucleotide "deoxy-A" overhang with a free 3'-OH is created on mutant heteroduplexes that are filled in with complementary dNTPs.

In contrast, wild-type heteroduplexes, partially protected heteroduplexes, and mutant heteroduplexes not filled in with complementary dNTPs remain blocked by the blocking adapter.

Preparation of a Reporter Adapter, Ligation of Full-Length Sequence Extended Products with the Reporter Adapter, and Release of Dual Adapter Ligation Products Two primers, E2F-TAA(+) 5'-GGCACTCGGCTGACAGTGTC-3' and E2F7(−) 5'-TGTGGTGTGGCTGCCCAG-3', derived from the E2F1 gene are employed to amplify a cDNA fragment (~160 bp) that contains a TAA-1 restriction enzyme site, ACAGT, as underlined in the forward primer E2F-TAA(+). Following treatment with TAA-1, the PCR fragment is digested into two smaller sub-fragments: a 145 bp subfragment carrying a single nucleotide "deoxy-T" overhang on its antisense strand and a 15 bp subfragment carrying a single nucleotide "deoxy-A" overhang on its sense strand. After size fractionation by gel electrophoresis, the 145 bp subfragment is purified and ready to be used as a reporter adapter. The reporter adapter (1 ng each) is then applied to each well for ligation in an optimized buffer (50 µl) containing 400 units of T4 DNA ligase at room temperature for 1 hour. The 3' single nucleotide "deoxy-T" overhang on the reporter adapter enables ligation only for full-length sequence extended products resulting from mutant heteroduplexes that are filled in with complementary dNTPs. Consequently, mutant-dual adapter hybrids are formed in mutant heteroduplexes filled in with complementary dNTPs while wild-type heteroduplexes, partially protected homologous heteroduplexes, and mutant heteroduplexes not filled in with complementary dNTPs remain blocked by the blocking adapter. By taking advantage of the Pst-1 site embedded in the blocking adapter, Pst-1 digestion is subsequently performed to release the dual adapter ligation products into supernatants for PCR amplification to detect low frequency mutants.

PCR Amplification of Dual Adapter Ligation Products and Identification of Mutants Semi-nested PCR is performed to amplify the dual adapter ligation products resulting from mutant heteroduplexes that are filled in with complementary dNTPs. The first round of PCR is carried out by using aforementioned Badp(+) and E2F7(−) as a forward primer and a reverse primer derived respectively from the blocking adapter and the reporter adapter. Following the first round of PCR, the second round of PCR is then performed using Badp(+) as a forward primer and another oligonucleotide E2F5(−), 5'-ACTGGATGTGGTTCTTGGAC-3', as a reverse primer. Primer E2F5(−) is derived from the sequence immediately 5' to the sequence of primer E2F7(−) on the E2F1 gene. The resulting semi-nested PCR product, Badp-E2F5, is ~135 bp in size. Of note is that the Badp-E2F5 PCR product spans a Sal-1 restriction enzyme site. Subjecting Badp-E2F5 PCR products to Sal-1 digest results in a detectable sub-fragment of ~110 bp and a ~25 bp sub-fragment that is frequently invisible by standard gel electrophoresis and ethidium bromide staining. Mutants are therefore identified by the presence of a 135 bp amplicon and confirmed by Sal-1 digest that creates a ~110 bp sub-fragment.

Dilution Experiments to Determine Assay Sensitivity

The total cellular RNA of a positive cell line, KG-1, is serially diluted into tenths and then mixed respectively with one microgram of the total cellular RNA of a negative control, resulting in a set of samples in various positives: 1, 1:10, $1:10^2$, $1:10^3$, $1:10^4$, $1:10^5$, and $1:10^6$. After subjecting these serially diluted samples to testing as described above, positives are identified by the presence of a 135 bp amplicon, Badp-E2F5. The sensitivity of the present method is therefore determined.

Results

Figure 6:
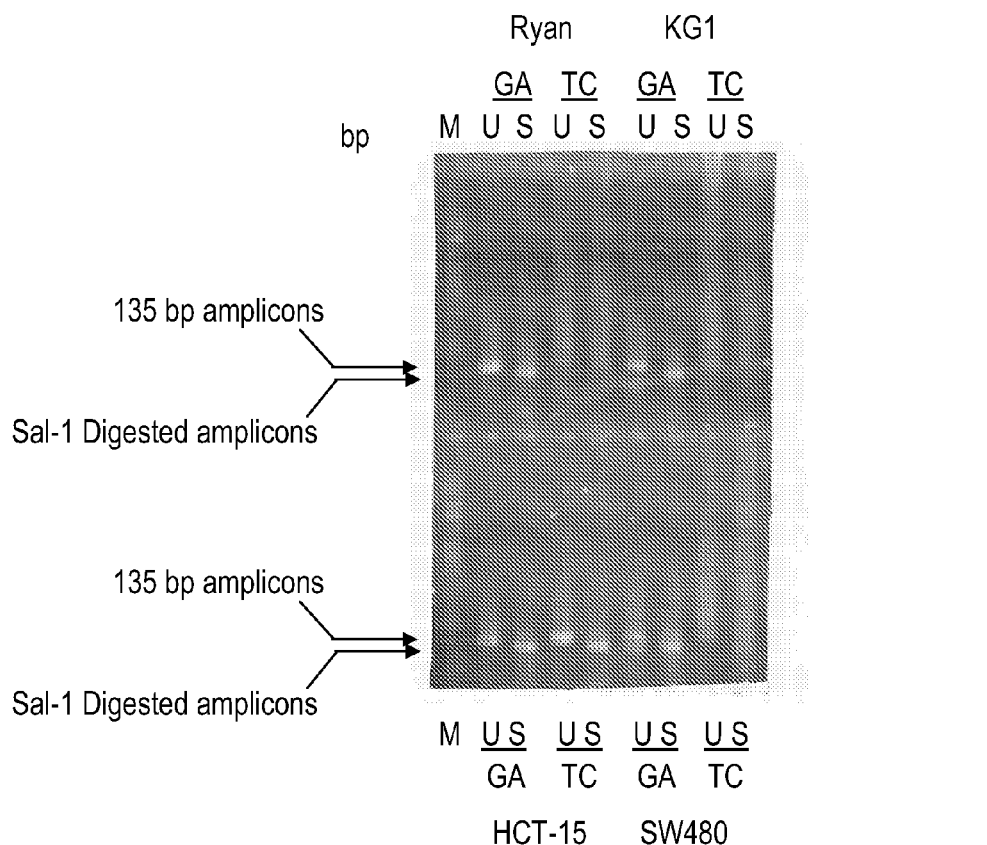
FIG. 6 shows representative results of a mutation detection method of the present disclosure.
Figure 7:
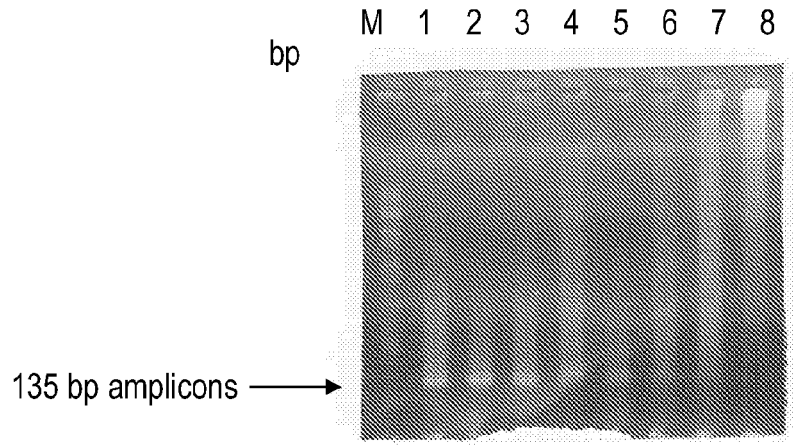
FIG. 7 shows the sensitivity of a mutation detection method of the present disclosure.

Ten different neoplastic cell lines and eight normal blood samples are tested for the presence of a mutation or mutations in nine target genes: K-ras, TP53, Erb-b2, VEGFR3, MSH6, CHEK2, BRIP1, LKB1, and PIK3CA. As expected, all of the eight negative control samples are negative. Also showing negative results are four neoplastic cell lines: MCF7 breast cancer cells, B15 lymphoblastic leukemia cells, HL-60 myeloid leukemia cells, and KBM7 myeloid leukemia cells. Positives are identified in the following: NCI-H460 lung cancer cells filled in by "GA," SW-480 colon cancer cells filled in by "GA," HCT-15 colon cancer cells filled in by "GA" and "TC," KG-1 myeloid leukemia cells filled in by "GA," HUT-78 T-cell leukemia cells filled in by "TC," and Ryan B-cell lymphoma cells filled in by "GA." Representatively shown in FIG. 6 are the results obtained from Ryan B-cell lymphoma cells (left four lanes of the upper panel), KG-1 myeloid leukemia cells (right four lanes of the upper panel), HCT-15 colon cancer cells (left four lanes of the lower panel), and SW-480 colon cancer cells (right four lanes of the lower panel). Positives are illustrated by the presence of Badp-E2F5 PCR amplicons of 135 bp in size (lanes "U") and confirmed by Sal-1 digestion (lanes "S") in Ryan lymphoma cells filled in by "GA," KG-1 myeloid leukemia cells filled in by "GA," HCT-15 colon cancer cells filled in by "GA" and "TC," and SW-480 colon cancer cells filled by "GA." To determine the sensitivity of the present method, analysis is carried out in a set of serially diluted samples harboring various concentrations of KG-1 leukemia cell RNA (1, 1:10, $1:10^2$, $1:10^3$, $1:10^4$, $1:10^5$, and $1:10^6$) and a negative control. Shown in FIG. 7 are the results of these samples in which DSF reactions are carried out using "GA." As shown in FIG. 7, Badp-E2F5 PCR amplicons of 135 bp are clearly detected in lanes 1~6, wherein KG-1 RNA is present at the dilution of 1, 1:10, $1:10^2$, $1:10^3$, $1:10^4$, and $1:10^5$, respectively. While there is no detectable band in the negative control (lane 8), a possible faint band might be present in lane 7 wherein KG-1 RNA is diluted to $1:10^6$. Taken together, these results indicate that the present assay permits simultaneous screening of a multitude of multiple different genes for the presence of a mutant or mutants among hundreds of thousands of normal cells.

Mutation Characterization by DNA Sequencing

DNA sequencing of the nine target genes in these 18 samples is performed. The mutations identified in the ten neoplastic cell lines tested are summarized in Table 2.

TABLE 2

| | Mutation Identified by Sequencing in Ten Neoplastic Cell Lines | | | | | | | | |
|---|---|---|---|---|---|---|---|---|---|
| | K-ras | TP53 | Erbb2 | VEGFR3 | MSH6 | CHEK2 | BRIP1 | LKB1 | PIK3CA |
| NCI-H460 | K061M AAG->ATG | WT | WT | WT | WT | WT | WT | WT | WT |
| HCT-15 | G013D GGA->GAC | S241F TCC->TTC | WT | WT | WT | WT | WT | WT | WT |
| SW-480 | G012V GGT->GTT | R273H CGT->CAT | WT | WT | WT | WT | WT | WT | WT |
| MCF7 | WT | WT | WT | WT | WT | WT | WT | WT | WT |
| KG-1 | WT | ·Insertion | WT | WT | WT | WT | WT | WT | WT |
| HL-60 | WT | WT | WT | WT | WT | WT | WT | WT | WT |
| KBM7 | WT | WT | WT | WT | WT | WT | WT | WT | WT |
| B15 | WT | WT | WT | WT | WT | WT | WT | WT | WT |
| HUT-78 | WT | R196X CGA->TGA | WT | WT | WT | WT | WT | WT | WT |
| Ryan | W019F T020S TTGACG ->TTTTCG | D281Y GAC->TAC | WT | WT | WT | WT | WT | WT | WT |

·Insertion of GATTC following the nucleotide "G" at nucleotide Position 922
WT: Wild-type
In each mutant, the nucleotide sequence change (lower line) is shown along with its involved codon and predicted amino acid change (upper line).

The results of DNA sequencing appear concordant with the results of the present DSF-applied mutation screening method. All positives as determined by the present DSF-applied method show the presence of a mutation or mutations in at least one of the nine target genes as detected by DNA sequencing. All negatives as determined by the present DSF-applied method also show negative results by DNA sequencing. Furthermore, the complementary dNTPs used for DSF to show positives match with the nucleotide sequence changes as identified by DNA sequencing. These findings confirm the specificity of the present DSF-applied mutation screening assay.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit to execute a method of simultaneously screening for genetic mutations in different genes in a multitude of samples, the kit comprising:
   an antisense deoxyribonucleic acid (DNA) probe, wherein the antisense DNA probe:
      includes an extra deoxyribonucleotide at the 5' end; and
      is configured to be mixed with a strand of a ribonucleic acid (RNA) to be tested to form a heteroduplex molecule within a sample;
   wherein the sample forms:
      a first population of fully hybridized wild-type heteroduplexes;
      a second population of mutant heteroduplexes having a single unhybridized ribonucleotide; and
      a third population of homologous heteroduplexes having at least one stretch of two or more unhybridized ribonucleotides; and
   a blocking adapter, wherein the blocking adapter:
      includes a dually phosphorylated sense strand; and
      is configured to protect a 3' end of the RNA strand.

2. The kit of claim 1 further comprising a user's guide comprising instructions for executing the method.

3. The kit of claim 1 further comprising:
   a ribonuclease enzyme, wherein the ribonuclease enzyme is configured to cleave the unhybridized ribonucleotides in the second population and the third population and exposes a 3' hydroxyl group at the cleavage sites.

4. The kit of claim 3 further comprising an RNA-primed DNA polymerase, wherein the RNA-primed DNA polymerase is configured to create a second sample performing differential sequence fill-in at the cleaved sites.

5. The kit of claim 4 further comprising:
   a single-strand-specific nuclease, wherein the a single-strand-specific nuclease is configured to digest unprotected deoxyribonucleotides in the third population and in the second population not filled in with a complementary dNTP;
   wherein the first population and heteroduplexes in the second population filled in with a complementary dNTP are undigested.

6. The kit of claim 5 further comprising:
   a DNA-dependent DNA polymerase, wherein the DNA-dependent DNA polymerase is used with all four dNTPs to create:
      a full-length sequence extension in the second population that has been filled in with a complementary dNTP; and
      a new 3' single nucleotide overhang carrying a free 3'-hydroxyl group that is unprotected.

7. The kit of claim 6 further comprising:
   a reporter adapter, wherein the reporter adapter;
      includes a tag; and
      is configured to link to the unprotected overhang to form marked mutant adapter hybrids.

8. The kit of claim 7 further comprising:
   reagent(s) for detecting, quantifying or amplifying said mutant adapter hybrids.

9. A kit to execute a method of simultaneously screening for genetic mutations in different genes in a multitude of samples, the kit comprising:
   an antisense deoxyribonucleic acid (DNA) probe, wherein the antisense DNA probe:
      includes an extra deoxyribonucleotide at the 5' end; and
      is configured to be mixed with a strand of a ribonucleic acid (RNA) to be tested to form a heteroduplex molecule within a sample;
   wherein the sample forms:
      a first population of fully hybridized wild-type heteroduplexes;
      a second population of mutant heteroduplexes having a single unhybridized ribonucleotide; and
      a third population of homologous heteroduplexes having at least one stretch of two or more unhybridized ribonucleotides; and
   a blocking adapter, wherein the blocking substrate adapter:
      includes a dually phosphorylated sense strand; and
      is configured to protect the 3' end of the RNA strand;
   an RNA-primed DNA polymerase, wherein the RNA-primed DNA polymerase is configured to create a second sample by performing differential sequence fill-in at cleaved sites; and
   a reporter adapter, wherein the reporter:
      includes a tag; and
      adapter is configured to link to the mutant heteroduplexes to form mutant-adapter hybrids.

10. The kit of claim 9 further comprising a second antisense DNA probe.

11. The kit of claim 9, wherein the antisense DNA probe includes target sequences selected from at least one of:
   genes;
   markers;
   nucleic acids that are associated with a disease;
   microorganisms that are associated with a disease;
   subtypes of a disease;
   a disease status;
   a medical condition;
   a cellular function; or
   a cellular function pathway.

12. The kit of claim 9 wherein at least one of:
the antisense DNA probe;
the blocking adapter;
the RNA-primed DNA polymerase; or
the reporter adapter;
includes a solid phase media.

13. The kit of claim 9, wherein the antisense DNA probe is immobilized on a substrate.

14. The kit of claim 13, wherein the antisense DNA probe is located at a specified location on the substrate.

15. A kit to execute a method of simultaneously screening for genetic mutations in different genes in a multitude of samples, the kit comprising:
- an antisense deoxyribonucleic acid (DNA) probe, wherein the antisense DNA probe:
  - includes an extra deoxyribonucleotide at the 5' end; and
  - is configured to be mixed with a strand of a ribonucleic acid (RNA) to be tested to form a heteroduplex molecule within a sample;
- wherein the sample forms:
  - a first population of fully hybridized wild-type heteroduplexes;
  - a second population of mutant heteroduplexes having a single unhybridized ribonucleotide; and
  - a third population of homologous heteroduplexes having at least one stretch of two or more unhybridized ribonucleotides; and
- a ribonuclease enzyme, wherein the ribonuclease enzyme is configured to cleave the unhybridized ribonucleotides in the second population and the third population and exposes a 3' hydroxyl group at the cleavage sites; and
- a blocking adapter, wherein the blocking adapter:
  - includes a dually phosphorylated sense strand; and
  - is configured to protect a 3' overhang on the RNA strand; and
- an RNA-primed DNA polymerase, wherein the RNA-primed DNA polymerase is configured to create a second sample by performing differential sequence fill-in at the cleaved sites; and
- a single-strand-specific nuclease, wherein the a single-strand-specific nuclease is configured to digest unprotected deoxyribonucleotides in the second sample; wherein the first population and heteroduplexes in the second population filled in with a complementary dNTP are undigested; and
- a DNA-dependent DNA polymerase, wherein the DNA-dependent DNA polymerase is used with all four dNTPs to create:
  - a full-length sequence extension in the second population that has been filled in with a complementary dNTP; and
  - a new 3' single nucleotide overhang carrying a free 3'-hydroxyl group that is unprotected; and
- a reporter adapter, wherein the reporter adapter:
  - includes a tag; and
  - is configured to link to the unprotected overhang to form marked mutant-dual adapter hybrids.

16. The kit of claim 15, wherein the tag includes at least one of:
a detectable substrate;
a quantifiable substrate; or
an amplifiable substrate.

17. The kit of claim 16 further comprising means for at least one of:
detecting the detectable substrate;
quantifying the quantifiable substrate; or
amplifying the amplifiable substrate.

18. The kit of claim 15 further comprising:
a sequence amplifier, wherein the sequence amplifier is configured to amplify a portion or the full length of the mutant-dual adapter hybrids.

19. The kit of claim 18 wherein said sequence amplifier includes at least one of:
a polymerase chain reaction amplifier;
a real-time polymerase chain reaction amplifier;
a ligase chain reaction amplifier;
a transcription-mediated amplifier; or
a polymerase chain reaction amplification followed by transcript amplifier.

20. The kit of claim 15 further comprising means for detecting dual adapter ligation products.

\* \* \* \* \*